(12) United States Patent
Kumar et al.

(10) Patent No.: US 10,206,872 B2
(45) Date of Patent: Feb. 19, 2019

(54) READY-TO-ADMINISTER SOLUTION OF FENTANYL CITRATE

(71) Applicant: SUN PHARMACEUTICAL INDUSTRIES LTD., Mumbai, Maharashtra (IN)

(72) Inventors: Samarth Kumar, Baroda (IN); Prashant Kane, Baroda (IN); Subhas Balaram Bhowmick, Baroda (IN); Milan Natvarbhai Thakkar, Baroda (IN); Kandarp Maheshkumar Dave, Baroda (IN)

(73) Assignee: SUN PHARMACUETICAL INDUSTRIES LTD., Mumbai, Maharashtra (IN)

( * ) Notice: Subject to any disclaimer, the term of this patent is extended or adjusted under 35 U.S.C. 154(b) by 0 days.

(21) Appl. No.: 15/185,452

(22) Filed: Jun. 17, 2016

(65) Prior Publication Data

US 2016/0367476 A1 Dec. 22, 2016

(30) Foreign Application Priority Data

Jun. 19, 2015 (IN) .......................... 2346/MUM/2015

(51) Int. Cl.
| | | |
|---|---|---|
| *A61K 31/4468* | (2006.01) | |
| *A61K 9/00* | (2006.01) | |
| *A61K 47/26* | (2006.01) | |
| *A61K 9/08* | (2006.01) | |

(52) U.S. Cl.
CPC .............. *A61K 9/0019* (2013.01); *A61K 9/08* (2013.01); *A61K 31/4468* (2013.01); *A61K 47/26* (2013.01)

(58) Field of Classification Search
CPC ......................... A61K 31/4468; A61K 9/0019
USPC ......................................................... 514/329
See application file for complete search history.

(56) References Cited

U.S. PATENT DOCUMENTS 5,948,389 A * 9/1999 Stein .................... A61K 9/0014
424/443

OTHER PUBLICATIONS

Royal Hospital for Women, Department Manual (2014): Fentanyl, p. 1.*
Eakins et al (Jun. 2005), BioProcess International, pp. 52-56. (Year: 2005).*
Pramanick et al, Pharma Times (Mar. 2013), vol. 45(3), pp. 65-77. (Year: 2013).*
West-Ward Pharmaceuticals Corp (1968), pp. 1-33. (Year: 1968).*

* cited by examiner

*Primary Examiner* — Jean P Cornet
*Assistant Examiner* — Janet L Coppins
(74) *Attorney, Agent, or Firm* — Sughrue Mion, PLLC

(57) ABSTRACT

A method of treating a patient in need of therapy with fentanyl or a salt thereof, the method comprising providing a ready-to-administer solution consisting essentially of fentanyl or a salt thereof as the sole active ingredient, a sugar or sugar alcohol and water for injection, the solution having a pH in the range of 3.5 to 7.5, and parenterally administering the solution to the patient.

8 Claims, No Drawings

READY-TO-ADMINISTER SOLUTION OF FENTANYL CITRATE

The present application claims benefit to Indian Patent Application No. 2346/MUM/2015, filed Jun. 19, 2015, the entire contents of which are incorporated herein by reference.

FIELD OF THE INVENTION

The present disclosure relates to a method of treating a patient in need of therapy with fentanyl or a salt thereof by providing a ready-to-administer solution of fentanyl or a salt thereof.

BACKGROUND OF THE INVENTION

Fentanyl, or its pharmaceutically acceptable salt, is an opioid receptor agonist. A preferred pharmaceutically acceptable salt of fentanyl is fentanyl citrate. The chemical name of fentanyl citrate is N-(1-phenylethyl)-4-piperidyl)-propionanilide citrate (1:1), which has the following structural formula:

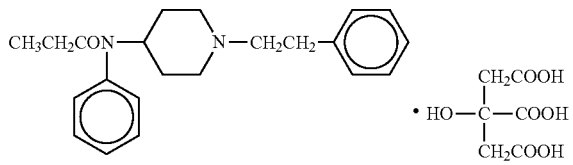

The approved products of fentanyl include tablets, lozenges (oral), transdermal patches and injectable solutions. Most of the injectable products of fentanyl currently available in the market contain sodium chloride, and these products, when intended for intravenous infusion, require dilution before administration using a suitable diluent, such as normal saline. For patients in need of therapy with fentanyl or a salt thereof, who also suffer from one or more conditions that are aggravated by increased plasma concentration of sodium ions, such as hypertension, hypernatremia, heart ailments such as congenital heart diseases, renal insufficiency, critical illness, and the like, it is important to avoid administration of sodium ions either as a constituent of the formulation or as a diluent. Because the currently available options involve the possibility of the use of preparations containing sodium ions, there always remains a chance that sodium ions may be accidentally administered to these patients. If proper care or attention is not taken and such patients are accidentally administered a preparation containing sodium ions, the patient's condition may be aggravated and become life threatening. There have been several reports of the accidental administration of sodium-containing preparations to patients who suffer from one or more conditions that get aggravated by an increased plasma concentration of sodium ions. Thus, there remains a need for a method of treating patients in need of therapy with fentanyl or a salt thereof, which method advantageously prevents or avoids the accidental infusion of preparations containing sodium to the patients who are in need of therapy with fentanyl or a salt thereof and who are also suffering from a condition which is aggravated by an increased plasma concentration of sodium ions.

SUMMARY OF THE INVENTION

The present disclosure provides a method of treating a patient in need of therapy with fentanyl or a salt thereof, said method comprising:

a. providing a ready-to-administer solution consisting essentially of fentanyl or a salt thereof as the sole active ingredient, sugar or sugar alcohol and water for injection, said solution having a pH in the range of 3.5 to 7.5; and b. parenterally administering the said solution to the patient.

The present disclosure also provides a sterile, ready-to-administer solution consisting essentially of fentanyl or a salt thereof as the sole active ingredient, a sugar or sugar alcohol and water for injection, said solution having a pH in the range of 3.5 to 7.5.

In another aspect, the present disclosure provides a sterile, ready-to-administer solution consisting essentially of fentanyl or a salt thereof as the sole active ingredient, a sugar or sugar alcohol and water for injection, said solution having a pH in the range of 3.5 to 7.5 for use in the treating a patient in need of therapy with fentanyl or a salt thereof, by parenterally administering the solution to the patient.

DETAILED DESCRIPTION OF THE INVENTION

The solution according to the present disclosure is suitable for direct parenteral administration, i.e., it is "ready-to-administer" meaning that the solution is prepared, filled into infusion container during manufacture, the solution is sterile and the parenteral administration does not require any steps or handling or manipulation before administration and can be directly administered parenterally to the patient. The solution of the present disclosure is premixed or ready to be administered and can be directly administered without the need for any intervening steps of reconstitution and/or dilution or mixing.

The term "consisting essentially of" denotes the nature of the solution used in the method of the present disclosure and is intended to mean a ready-to-administer solution that does not include a sodium ion containing excipient other than sodium hydroxide and/or a buffer component for example, sodium hydrogen phosphate which may be used, if required, in amounts sufficient to adjust the pH. The term "consisting essentially of" is intended to mean a ready-to-administer solution that does not include mucoadhesive components such as pectins or alginates or chitosan and the like; or surfactants or emulsifiers such as tweens, polysorbates, poloxamers and the like. The term "consisting essentially of" is further intended to mean a ready-to-administer solution that does not include a water miscible organic solvent such as ethanol, propylene glycol and the like. Accordingly, in an embodiment, the present disclosure pertains to a method that does not include the administration of sodium, other than sodium hydroxide and/or a buffer component for example, sodium hydrogen phosphate which may be used, if required, in amounts sufficient to adjust the pH.

The ready-to-administer solution according to the present disclosure does not include pectin or chitosan. In one or more embodiments, the ready-to-administer solution according to the present disclosure does not include surfactants like tweens, polysorbates, poloxamers. In one or more embodiments, the ready-to-administer solution according to the present disclosure does not include organic solvents such as ethanol, propylene glycol.

Impurity A as used herein is a degradation impurity and is N-phenyl-N-[cis, trans-1-oxido-1-(2-phenylethyl)piperidin-4-yl]propanamide. The chemical structure of impurity A is given below:

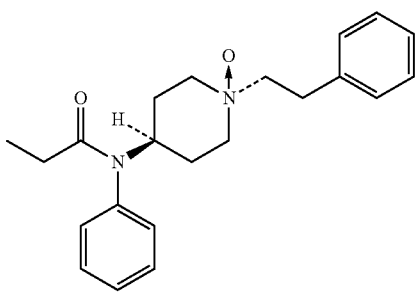 [SMILES: CCC(=O)N(c1ccccc1)[C@H]1CC[N@+]([O-])(CCc2ccccc2)CC1]

Impurity B as used herein is N-phenyl-N-(piperidin-4-yl) propanamide and is structurally represented by the following structure:

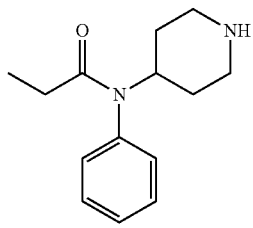 [SMILES: CCC(=O)N(c1ccccc1)C1CCNCC1]

Impurity C as used herein is N-Phenyl-n-[1-(2-phenyl-ethyl)-4-piperidinyl]acetanilide, a potential synthetic impurity and is structurally represented by the following structure:

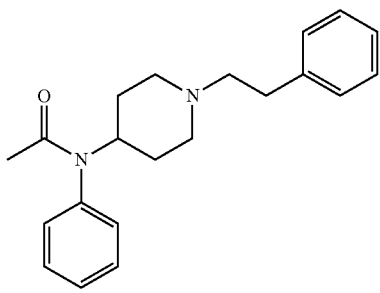 [SMILES: CC(=O)N(c1ccccc1)C1CCN(CCc2ccccc2)CC1]

Impurity D as used herein is N-Phenyl-1-(2-phenylethyl)-4-piperidinamine and is structurally represented by the following structure:

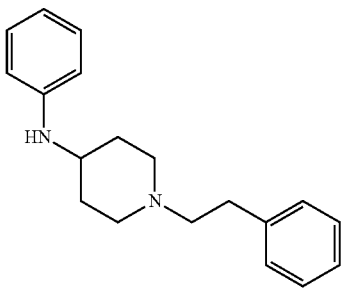 [SMILES: c1ccc(CCN2CCC(Nc3ccccc3)CC2)cc1]

The present disclosure provides a method of treating a patient in need of therapy with fentanyl or a salt thereof, said method comprising (a) providing a ready-to-administer solution consisting essentially of fentanyl or a salt thereof as the sole active ingredient, a sugar or sugar alcohol and water for injection, said solution having a pH in the range of 3.5 to 7.5; and (b) parenterally administering the solution to the patient.

The method of the present disclosure presents an advantage in that it prevents or avoids accidental infusion of preparations containing sodium to patients who are in need of therapy with fentanyl or a salt thereof but who are also suffering from a condition which is aggravated by increased plasma concentration of sodium ions. Accidental infusion of a preparation containing sodium can occur in several instances, including as a result of accident or error by a medical practitioner or hospital care individuals, to patients who are contraindicated for sodium ion intake. Contraindications may exist in patients suffering from, e.g., hypertension or hypernatremia, patients in medical surgical hospitals suffering from hypernatremia, or patients suffering from congenital heart disease, renal insufficiency, critical illness and the like. Such accidental administration can happen as a result of either ignorance or unawareness. The injectable infusion products of fentanyl currently available in the market contain sodium chloride, and these products when intended for intravenous infusion, require dilution before administration, as they are not ready-to-administer. Therefore, there always remains a chance of accidental administration of preparations containing large quantities of sodium ions, such as is present in a normal saline diluent, to patients such as those discussed above. Particularly, in case when large volume of solution is required in indications such as general anaesthesia, post-operative pain control etc., there are chances of administering huge amounts of sodium chloride if the product itself contains sodium chloride or requires a diluent containing sodium chloride. This accidental administration can lead to the aggravation of the patient's condition, which can have life threatening consequences. The ready-to-administer solution of the present disclosure, which is devoid of sodium other than sodium hydroxide and/or a buffer component, for example, sodium hydrogen phosphate which may be used, if required, in amounts sufficient to adjust the pH, and which does not require the use of any diluent before administration, will avoid such errors or accidents, which may be otherwise a huge concern, especially for administration during critical care or during critical conditions, such as a patient undergoing surgery or the like. The method of the present invention avoids such administration. The present disclosure provides a method of treating patients in need of therapy with fentanyl or a salt thereof, which method also prevents or avoids the accidental infusion of preparations containing sodium to the patients. The method of treatment according to the present disclosure is suitable for treatment of patients in need of therapy with fentanyl or a salt thereof, for instance patients suffering from pain, patients undergoing a surgical procedure, as an adjunct to general anesthesia, as an adjunct to regional anesthesia, as a general anesthesia, or as premedication. For patient undergoing surgical procedure, the ready-to-administer solution may be given before, during and after surgical procedure.

The ready-to-administer solution of the present invention is suitable for direct parenteral administration. The parenteral administration routes suitably include, but are not limited to, intravenous infusion or injection, intramuscular, intra-arterial, subcutaneous and the like.

In one embodiment the ready-to-administer solution does not contain or is free of sodium or sodium ions, other than sodium hydroxide and/or a buffer component, for example, sodium hydrogen phosphate which may be used, if required, in amounts sufficient to adjust the pH.

In one embodiment the solution does not contain pectin. In one embodiment the solution does not contain chitosan. In one embodiment the solution does not contain poloxamer and other surface active agents like tween or polysorbate. In one embodiment the solution does not contain benzalkonium chloride. In one embodiment the solution does not contain ethanol and propylene glycol.

In one embodiment the solution does not contain an additional diluent. In one embodiment the method does not require a dilution step.

Fentanyl or a salt thereof as used herein includes pharmaceutically acceptable salts of fentanyl. Examples of suitable pharmaceutically acceptable salts of fentanyl for use in accordance with the present disclosure include for example, but not limited to citrate, hydrochloride, chloride, sulphate, tartrate, or other similar salt forms. In certain embodiments, the fentanyl may be employed as the free base in the ready-to-administer solution of the present disclosure. In preferred embodiments, the pharmaceutically acceptable salt of fentanyl is fentanyl citrate.

The method of treating a patient in need of therapy with fentanyl or a salt thereof according to the present disclosure comprises ready-to-administer solution of fentanyl or a salt thereof, said solution containing fentanyl or a salt thereof as the sole active ingredient in an amount ranging from about 0.001 mg/ml to about 0.1 mg/ml, such as about 0.005, 0.01, 0.015, 0.02, 0.025, 0.03, 0.035, 0.04, 0.045, 0.05, 0.055, 0.06, 0.065, 0.07, 0.075, 0.08, 0.085, 0.09 or 0.095 mg/ml, preferably from about 0.005 mg/ml to 0.075 mg/ml, more preferably from about 0.01 mg/ml to about 0.05 mg/ml. Suitably, the amount of fentanyl or its salt used in the present disclosure is expressed as amounts equivalent to fentanyl base. In one embodiment, the ready-to-administer solution contains from about 0.001 mg/ml to about 0.1 mg/ml of fentanyl citrate. In one preferred embodiment, the ready-to-administer solution contains 0.01 mg/ml of fentanyl citrate. In another preferred embodiment, the ready-to-administer solution contains 0.05 mg/ml of fentanyl citrate.

According to one embodiment, the ready-to-administer solution may be provided in volumes ranging from small volumes to large volumes, such as from about 1 ml to 1000 ml, such as about 10, 50, 100, 150, 200, 250, 300, 350, 400, 450, 500, 550, 600, 650, 700, 750, 800, 850 or 900 ml. When the solution is provided in small volumes, it may be filled into containers such as vials, syringes, ampoules, auto-injectors, prefilled syringes and similar packaging systems. Typically, in some embodiments, the volumes range from 1 ml to 50 ml, such as about 5, 10, 15, 20, 25, 30, 35, 40 or 45 ml, preferably 2 ml to 30 ml. However, it is possible to present the ready-to-administer solution of the present invention in different volumes by adjusting the concentration of fentanyl or a salt thereof.

Alternatively, when the solution is provided in large volumes, it may be it filled into containers such as infusion bags, bottles, pouches, large volume prefilled syringes, and such similar packaging systems. Typically, in some embodiments, the volumes range from 50 ml to 1000 ml, preferably, 50 ml to 500 ml, such as 60, 70, 80, 90, 100, 150, 200, 250, 300, 350, 400 or 450 ml. Preferred embodiments include volumes of the solution filled into containers in the range of 100 ml to 300 ml. In one preferred embodiment, the volume is 100 ml. In another preferred embodiment, the volume is 250 ml. However, it is possible to present the ready-to-administer solution of the present disclosure in different volumes by adjusting the concentration of fentanyl or a salt thereof. For example, in one specific embodiment, the amount of fentanyl or a salt thereof ranges from 0.005 mg/ml to 0.075 mg/ml and is present in large volumes ranging from 50.0 ml to 500 ml.

According to the present disclosure, the ready-to-administer solution used in the method of the present disclosure is contained in a container suitable for parenteral administration. The container used according to the present disclosure may be an infusion bag, infusion bottle, a flexible pouch, a prefilled syringe, and the like. In some embodiments, the container may be a syringe, a vial or an ampoule. The container may be of variable size or volume.

The containers used to hold the solution may be made up of glass or polymeric materials. It is possible to use a glass which has been coated with a barrier/polymer. In one preferred embodiment, the container is made up of a material which comprises a polymer of a cyclic olefin.

The polymer of a cyclic olefin may be a cycloolefin homopolymer (COP) or a cycloolefin copolymer (COC) or a mixture thereof. Cycloolefin homopolymers (cycloolefin polymers, or COP) are homopolymers comprising single type of cycloolefin monomers. Cycloolefins (cyclic olefins) are mono or polyunsaturated, mono or polycyclic ring systems such as cycloalkenes (like cyclopropene, cyclopentene, cyclobutene, cyclohexene), bicycloalkenes (like norbornene, dicyclopentadiene), tricycloalkenes, tetracycloalkenes (tetracyclododecene) and the like. The ring system can be monosubstituted or polysubstituted. Cycloolefin copolymers (COC) comprise cycloolefins and co-monomers, wherein cycloolefins are copolymerized with one or more comonomers. Suitable co-monomers are unsubstituted or substituted olefins, of 2 to 20 carbon atoms, preferably 2 to 6 carbon atoms, such as ethylene, propylene, butene, hexene. Any of these olefins may be used individually, or two or more types of olefins may be used in combination. In one or more embodiments of the present disclosure, the container may comprise one or more layers, wherein at least a portion of the inside wall of the container, i.e. the inner layer, comprises a polymer of cycloolefin. The container additionally may have layers on the outer side which may be another layer of polymer of cycloolefin or a layer of another polymer, such as for example, a polyethylene polymer, low density polyethylene, linear low density polyethylene. In one embodiment, the container may comprise a first portion including a first polymer that forms the inner surface of the container and a second portion including a second polymer that forms the outer surface of the container. The first polymer and the second polymer layer may be directly bondable to each other as such or through a third polymer that is bondable to the first and second polymer and fixedly secures the first and second portions to each other. In some embodiments, the first and second polymer or the first, second, and third polymers layers are co-extruded or moulded. In some embodiments, the first and second portions may be non-bondable and one of these may be flexible, while the other may be rigid. The polymer that forms the inner surface/layer of the container that remains in contact with the solution of fentanyl or a salt thereof is preferably cycloolefin-based. In one preferred embodiment, the container is an infusion bag wherein at least a portion of the inside wall of the container is made up of polymer of a cyclic olefin selected from cycloolefin homopolymer or cycloolefin copolymer.

According to one preferred embodiment of the present disclosure, the container may be over wrapped with a secondary packaging. The secondary packaging may comprise a second container, such as a pouch or overwrap or carton. The secondary packaging may comprise a suitable pouch, such as an aluminum pouch covering the infusion container. The overwrap pouch may have a layer of oxygen absorbing material or alternatively the secondary packaging may comprise an oxygen scavenger that may be placed in between the infusion container and overwrap/pouch. In one preferred embodiment, the secondary packaging comprises both an aluminum pouch and an oxygen scavenger.

Preferably, the concentration of the fentanyl or a salt thereof and the volume of solution in the infusion containers is such that it allows direct infusion of the solution so as to deliver the required dose to the patient, without any intervening steps of dilution or reconstitution. The presentation of a ready-to-administer solution provides advantages over the existing products of fentanyl in which the solution may require further dilution before administration. The present disclosure, in one embodiment, provides a kit with containers having different volumes of solution of fentanyl or a salt thereof so that low, moderate and high doses of fentanyl may be injected without the step of dilution. In one embodiment, the present disclosure provides a kit with plurality of containers having one set of large volume containers and further sets of small volume top-up containers filled with solution of fentanyl or a salt thereof at same or different concentrations, such that one or more container(s) from the first set and if required one or more top-up container(s) from the second or further third set, directly administers the desired dose of fentanyl calculated based on body weight and approved indication. According to one embodiment of the present invention, the ready-to-administer solution is present in a plurality of containers comprising larger and smaller containers, wherein a concentration of fentanyl or a salt thereof is greater in the smaller containers than in the larger containers, and wherein the desired dose is administered simultaneously or sequentially from the plurality of containers. The following table provides an example of dosages that may be used for certain indications.

| Indication | Dose | Dose in mcg/kg | Total Dose For 70 kg person Dose in mcg | Volume administered 50 mcg/ml solution | Volume administered 10 mcg/ml solution |
|---|---|---|---|---|---|
| Adjunct to general anaesthesia | Low Dose | 2.0 | 140 mcg | 2.8 mL | 14 ml |
| | Moderate dose | 2 to 20 | 140 to 1400 mcg | 2.8 to 28 ml | 14 to 140 ml |
| | High dose | 20 to 50 | 1400 to 3500 mcg | 28 to 70 ml | 140 to 350 ml |
| General Anaesthesia | Dose | 50 to 100 to 150 | 3500 to 7000 to 10500 mcg | 70 to 140 ml to 210 ml | 350 to 700 ml to 1050 ml |

Further, the infusion rate may vary from 0.7 mcg/kg/hour to 10 mcg/kg/hour, such as 0.8, 0.9, 1.0, 1.5, 2.0, 2.5, 3.0, 3.5, 4.0, 4.5, 5.0, 5.5, 6.0, 6.5, 7.0, 7.5, 8.0, 8.5, 9.0 or 9.5 mcg/kg/hour. For a patient of 70 kg weight the amount of drug required in 24 hours, i.e., one day, may respectively vary from 1176 mcg to 16800 mcg.

In one embodiment, 117.6 ml to 1680 ml of a 10 mcg/ml solution according to the present disclosure will cater to the dose required. In another embodiment, 23.52 ml to 336 ml of a 50 mcg/ml solution according to the present disclosure will cater to the dose required. Infusion bags filled with different volumes of the solution having same or different concentrations can be combined to administer the desired dose with acceptable variation. For instance, to administer drug at 5 mcg/kg/hour, 8400 mcg drug would be required in 24 hours. This can be suitably administered using a 100 ml bag of 50 mcg/ml drug solution (=5000 mcg)+250 ml of 10 mcg/ml drug solution (=2500 mcg)+100 ml of a 10 mcg/ml drug solution (=1000 mcg).

According to another aspect, the present disclosure also provides a sterile, ready-to-administer solution consisting essentially of fentanyl or a salt thereof as the sole active ingredient, a sugar or sugar alcohol and water for injection, said solution having a pH in the range of 3.5 to 7.5.

According to yet another aspect, the present disclosure provides a sterile, ready-to-administer solution consisting essentially of fentanyl or a salt thereof as the sole active ingredient, a sugar or sugar alcohol and water for injection, said solution having a pH in the range of 3.5 to 7.5 for use as a medicament.

In one embodiment, the present disclosure provides a sterile, ready-to-administer solution consisting essentially of fentanyl or a salt thereof as the sole active ingredient, a sugar or sugar alcohol and water for injection, said solution having a pH in the range of 3.5 to 7.5 for use in the treating a patient in need of therapy with fentanyl or a salt thereof, by parenterally administering the solution to the patient.

In one embodiment, the present disclosure provides a sterile, ready-to-administer solution of fentanyl or a salt thereof for use as an analgesic.

The ready-to-administer solution of fentanyl or a salt thereof according to the method of the present disclosure includes a sugar or sugar alcohol. The sugar that is used in the solution according to the method of the present disclosure is selected from dextrose, glucose, fructose, sucrose, lactose, trehalose, and the like and mixtures thereof. The sugar alcohol used in the solution according to the method of the present disclosure is selected from mannitol, sorbitol, inositol, xylitol and the like and mixtures thereof. Preferably, in one embodiment the ready-to-administer solution of fentanyl or a salt thereof includes a sugar such as dextrose or glucose. Dextrose or glucose may be present in the solution in an amount ranging from about 40 mg/ml to about 80 mg/ml, such as about 45, 50, 55, 60, 65, 70 or 75 mg/ml, preferably in an amount ranging from about 50 mg/ml to about 75 mg/ml. In one preferred embodiment, dextrose is present in the solution in an amount of 50 mg/ml. In another embodiment, the ready-to-administer solution of fentanyl or a salt thereof includes a sugar alcohol such as mannitol or sorbitol. In one embodiment, the mannitol may be present in the solution in an amount ranging from about 45 mg/ml to about 70 mg/ml, such as about 50, 55, 60 or 65 mg/ml, preferably about 50 mg/ml. The sugar or sugar alcohol provides the solution that is iso-osmolar and is chemically stable. The osmolality of the solution is in the range of about 250-375 mOsm/kg, such as about 260, 270, 280, 290, 300, 310, 320, 330, 340, 350, 360 or 370 mOsm/kg, preferably in the range of 250-320 mOsm/kg. The sugar or sugar alcohol according to the present disclosure does not include sodium other than sodium hydroxide and/or a buffer component for example, sodium hydrogen phosphate which may be used, if required, in amounts sufficient to adjust the pH The pH of the ready-to-administer solution of fentanyl or a salt thereof, used in the method of the present disclosure is in the range of about 3.5 to 7.5, such as about 4.0, 4.5, 5.0, 5.5, 6.0, 6.5 or 7.0, preferably between 3.5 to 6.0, most preferably between 3.5 to 5.5. In one embodiment, the pH of the solution is achieved and maintained in this range without the use of any pH adjusting agent. In other embodiments, a suitable pH adjusting agent and/or a buffer component may be used, if required, to adjust the pH in a desired range. The pH adjusting agent that may be used, if required, is selected from hydrochloric acid, citric acid, acetic acid, tartaric acid, tromethamine, potassium hydroxide, sodium hydroxide and the like and mixtures thereof. In preferred embodiments, the ready-to-administer solution is free of a pH adjusting agent or buffering agent.

In one preferred embodiment, the present disclosure provides a sterile, ready-to-administer solution consisting essentially of fentanyl citrate as the sole active ingredient, a sugar or sugar alcohol and water for injection, the solution having a pH in the range of 3.5 to 7.5 and the fentanyl citrate having a concentration in the range of 0.005 to 0.1 mg/ml.

In one embodiment, the present disclosure provides a sterile, ready-to-administer solution consisting essentially of fentanyl citrate as the sole active ingredient, a sugar selected from dextrose, glucose or fructose, and water for injection, the solution having a pH in the range of 3.5 to 7.5 and the fentanyl citrate having a concentration in the range of 0.005 to 0.1 mg/ml.

In one embodiment, the present disclosure provides a sterile, ready-to-administer solution consisting essentially of fentanyl citrate as the sole active ingredient, dextrose and water for injection, the solution having a pH in the range of 3.5 to 5.5 and the fentanyl citrate having a concentration in the range of 0.005 to 0.075 mg/ml.

In one embodiment, the present disclosure provides a sterile, ready-to-administer solution consisting essentially of fentanyl citrate as the sole active ingredient, sugar alcohol selected from mannitol or sorbitol, and water for injection, the solution having a pH in the range of 3.5 to 7.5 and the fentanyl citrate having a concentration in the range of 0.005 to 0.1 mg/ml.

In one preferred embodiment, it was found that the ready-to-administer solution consisting essentially of fentanyl citrate, dextrose, water and having a pH in the range of 3.5 to 5.5, showed better stability as compared to solutions that are devoid of dextrose/tonicity adjusting agents or solutions that contain other tonicity adjusting agents, such as sodium chloride.

The ready-to-administer solution of fentanyl or a salt thereof used in the method of the present disclosure is physically and chemically stable when stored at room temperature for at least 12 months. The solution is chemically stable in that the assay of the drug remains within the specified limit (90-110%) and content of related compounds or impurities remains within a specified limit, i.e., impurity A, B, C and D are not present in amounts of more than 0.5% by weight, the highest unknown impurity is not more than 0.2% by weight, and the total impurities is not more than 0.5% by weight, upon storage at room temperature for the shelf life period of at least 12 months. In preferred embodiments, the assay values remain within the specified limit upon storage at room temperature until 18 months, preferably until 24 months.

The ready-to-administer solution used in the method of the present disclosure is sterile. The term "sterile" or 'sterilized', as used in the context of the present disclosure, means a solution that has been brought to a state of sterility and has not been subsequently exposed to microbiological contamination, i.e., the sterility of the solution present in the container has not been compromised. The solution complies with the sterility requirements of the standard Pharmacopoeias, such as the United States Pharmacopoeia (USP). Sterilization may be achieved by suitable techniques, such as filtration sterilization, radiation sterilization, or autoclaving. In one preferred embodiment, the ready-to-administer solution of the present disclosure is subjected to membrane filtration followed by filling into a suitable container and terminal sterilization by autoclaving. In one embodiment, the ready-to-administer solution present in one or more containers is terminally sterilized by moist heat sterilization. In one embodiment, the ready-to-administer solution present in one or more containers has been sterilized by autoclaving. The autoclaving is preferably carried out at 121° C. for 15 minutes. In one or more embodiments, the autoclaving may be carried out at temperatures varying from about 110° C. to 125° C. for a period of time varying from about 5 minutes to 60 minutes. It was observed that the ready-to-administer solution of the present disclosure contained in infusion container withstands the extreme conditions of autoclaving and remains stable, physically and chemically, even upon being subjected to autoclaving and subsequent storage.

According to one aspect of the present disclosure, there is provided a process for the manufacture of a ready-to-administer solution of fentanyl as per the present invention, the process comprising the steps of:
  a) preparing a solution of fentanyl or a salt thereof and a sugar or a sugar alcohol in water;
  b) adjusting the pH of the solution in the range of 3.5 to 7.5;
  c) filtering the solution of step b);
  d) filling the solution aseptically into an infusion container; and
  e) sterilizing the solution of step d).

In specific embodiments, the process involves the steps of purging nitrogen into water for injection to attain a dissolved oxygen level of less than 1 ppm, adding dextrose into the water for injection, followed by the addition of fentanyl or a salt thereof to the above solution and checking the pH of the solution. If the pH is outside the range of 3.5 to 7.5, a suitable pH adjusting agent may be added so as to adjust the pH to the desired range. Further steps include filtration of the above solution using a membrane filter and aseptically filling the solution into an infusion container, such as an infusion bag, followed by terminally sterilizing the filled containers in an autoclave at 121° C. for 15 minutes. The process further optionally includes wrapping the filled infusion container with an aluminum pouch, along with the use of an oxygen scavenger.

In the context of this specification "comprising" is to be interpreted as "including".

Aspects of the invention comprising certain elements are also intended to extend to alternative embodiments "consisting" or "consisting essentially" of the relevant elements.

Where technically appropriate, embodiments of the invention may be combined.

Embodiments are described herein as comprising certain features/elements. The disclosure also extends to separate embodiments consisting or consisting essentially of said features/elements.

Technical references such as patents and applications are incorporated herein by reference.

Any embodiments specifically and explicitly recited herein may form the basis of a disclaimer either alone or in combination with one or more further embodiments.

Hereinafter, embodiments of the present disclosure will be more specifically described by way of examples. The examples should not be understood as limiting the scope of the present disclosure, and are merely used as illustrations of specific embodiments of the present disclosure.

Examples 1 and 2

Ready-to-administer solutions of fentanyl citrate according to specific embodiments of the present disclosure are given below in Table 1.

TABLE 1

Ready-to-administer solutions of fentanyl citrate.

| Ingredients | amount in mg/ml | |
|---|---|---|
| | Example 1 | Example 2 |
| Fentanyl Citrate eq. to Fentanyl Base | 0.05 | 0.01 |
| Dextrose, monohydrate | 50.0 | 50.0 |
| Water for Injection | q.s. to 1 ml | q.s. to 1 ml |

Water for injection was purged with nitrogen to attain a dissolved oxygen level of less than 1 ppm. Dextrose was added to the water for injection and dissolved. Purging with nitrogen was continued. Fentanyl citrate was then added to the above solution. The pH of the solution was checked and it was kept in the range of pH 3.5 to 5.5 by adding a suitable pH adjusting agent when required. The solution was filtered through a 0.2 micron membrane filter and was filled into an infusion container (a bag) made from a cycloolefin polymer. The filled infusion container was then terminally sterilized in an autoclave at 121° C. for 15 minutes. The infusion container was over wrapped with an aluminum pouch along with an oxygen scavenger. This was charged for a stability study and the assay value as well as known and highest unknown impurity and total impurities were measured periodically. The total impurities, known impurities including Impurity A, B, C and Impurity D and any individual unknown impurity were analyzed by HPLC or high performance liquid chromatography method. The mobile phase was a mixture of potassium dihydrogen orthophosphate (a buffer having a pH of about 3.2), acetonitrile and methanol; the chromatographic column was Inertsil ODS 3V (250×4.6) mm 5μ column and the chromatograms were recorded using UV spectroscopy. The assay of drug was also analysed by HPLC or high performance liquid chromatography method. The mobile phase was a mixture of ammonium acetate buffer (having a pH of about 3.2), methanol, acetonitrile and glacial acetic acid; the chromatographic column was Inertsil ODS 3V (250×4.6) mm 5μ column and the chromatograms were recorded by UV spectroscopy using a ultraviolet spectrophotometer.

The percentage transmittance of the solution was measured by UV (ultraviolet) spectroscopy using a UV spectrophotometer at a wavelength of 650 nm, wherein the transmittance of 1 cm layer of sample at 650 nm was measured using a suitable UV spectrophotometer against water blank. The pH of the solution was measured by a calibrated pH meter at 25° C.±2° C. The osmolality of the solution was measured by an osmometer.

The results for stability testing at various time points upon storage of the solution of Example 1, at 25° C. and 40° C. are shown below in Table 2.

TABLE 2

Observations of stability testing:

| Storage Condition | Time (M) | Assay of fentanyl Limit 90-110% | Imp. A NMT 0.5% | Imp. B NMT 0.5% | Imp. C NMT 0.5% | Imp. D NMT 0.5% | Highest Unknown Imp. NMT 0.2% | Total Imp. NMT 0.5% | % T @ 650 nm NLT 95% | Osmolality (mOsm) 250-350 |
|---|---|---|---|---|---|---|---|---|---|---|
| 25° C. | 0 M | 100.06 | ND | 0.004 | ND | ND | 0.008 | 0.019 | 100 | 265 |
| 40% relative humidity | 12 M | 102.13 | ND | ND | ND | ND | 0.013 | 0.017 | 98.851 | 272 |
| 40° C. | 1 M | 101.73 | ND | 0.013 | ND | ND | 0.046 | 0.059 | 100 | 268 |
| 25% relative humidity | 6 M | 101.14 | ND | 0.005 | ND | ND | ND | 0.005 | 100 | 269 |

M—Month;
Imp.—Impurity;
% T—% Transmittance;
NMT—Not more than;
NLT—Not Less than;
ND—Not detected The results for stability testing upon storage of the solution of Example 2, at 25° C. and 40° C. are shown below in Table 3.

TABLE 3

Observations of stability testing:

| Storage Condition | Time (M) | Assay of fentanyl Limit 90-110% | Imp. A NMT 0.5% | Imp. B NMT 0.5% | Imp. C NMT 0.5% | Imp. D NMT 0.5% | Highest Unknown Imp. NMT 0.2% | Total Imp. NMT 0.5% | % T @ 650 nm NLT 95% | Osmolality (mOsm) 250-350 |
|---|---|---|---|---|---|---|---|---|---|---|
| 25° C.; 40% relative humidity | 0 M | 99.7 | ND | 0.003 | ND | ND | 0.019 | 0.022 | 99.709 | 272 |
|  | 12 M | 101.51 | ND | ND | ND | ND | 0.036 | 0.045 | 100 | 274 |
| 40° C.; 25% relative humidity | 1 M | 101.71 | ND | 0.006 | ND | ND | 0.009 | 0.015 | 100 | 271 |
|  | 6 M | 100.58 | ND | 0.01 | ND | ND | ND | 0.01 | 99.916 | 274 |

M—Month;
Imp.—Impurity;
% T—% Transmittance;
NMT—Not more than;
NLT—Not Less than;
ND—Not detected As can be seen from Tables 2 and 3 above, the ready-to-administer solutions of fentanyl citrate of the present disclosure, when filled, autoclaved, and stored in an infusion container, remained physically and chemically stable upon storage at room temperature (25° C.; 40% relative humidity) for at least 12 months. There occurred no drop in the assay of fentanyl citrate and no substantial increase in the impurities level, and the values remained within the desired specified limits. It was observed that the assay of fentanyl remained almost unchanged upon storage, wherein the values are maintained within the range of 95%-105%. The total impurities remained less than 0.1% by weight of fentanyl; the highest unknown impurity remained less than 0.1% by weight and other known impurities (Impurity A, B, C, D) were either undetected or remained below 0.1% by weight. Further, it was observed that the solution remained physically stable, such that no precipitation or crystallization or color change took place upon storage, and the value of the percentage transmittance of the solution remained greater than 90%, preferably greater than 95% upon long term storage at room temperature. Surprisingly, the solution also remained chemically stable upon storage at the accelerated stability testing condition of 40° C., 25% relative humidity for a period of 6 months, which correlates to a room temperature shelf life stability for 24 months. The ready-to-administer solution of fentanyl citrate according to the present disclosure thus shows long term stability and room temperature shelf life stability of 24 months.

We claim:

1. A method of administering anesthesia and/or analgesia to a patient by parenterally administering fentanyl or a salt thereof, said method comprising:
    a. providing a ready-to-administer solution consisting essentially of fentanyl or a salt thereof as the sole active ingredient, a sugar or sugar alcohol, and water for injection, wherein said solution has a pH in the range of 3.5 to 7.5, has a volume from 50 ml to 500 ml in an infusion container, has been sterilized by autoclaving, and is physically and chemically stable when stored at room temperature for at least 12 months; and
    b. parenterally administering said solution to a patient selected from the group consisting of a patient undergoing a surgical procedure, a patient in need of fentanyl as an adjunct to regional or general anesthesia, and a patient in need of fentanyl as a general anesthetic,
    wherein the solution is directly administered intravenously to the patient and does not require any intervening steps of reconstitution and/or dilution or mixing.

2. The method as claimed in claim 1, wherein the sugar is selected from the group consisting of dextrose, glucose, fructose or mixtures thereof.

3. The method as claimed in claim 1, wherein the sugar alcohol is selected from the group consisting of mannitol or sorbitol or mixtures thereof.

4. The method as claimed in claim 1, wherein the solution is present in one or more containers, and fentanyl or a salt thereof is present in amount ranging from 0.001 mg/ml to 0.1 mg/ml.

5. The method as claimed in claim 4, wherein fentanyl or a salt thereof is present in an amount ranging from 0.005 mg/ml to 0.075 mg/ml.

6. The method as claimed in claim 4, wherein the container comprises a polymer of a cyclic olefin.

7. The method as claimed in claim 1, wherein the infusion container is an infusion bag made from polymeric material.

8. The method as claimed in claim 1, wherein the polymeric material is a cyclic olefin.

* * * * *